(12) United States Patent
Inoue et al.

(10) Patent No.: US 9,709,382 B2
(45) Date of Patent: Jul. 18, 2017

(54) LIGHT SOURCE APPARATUS AND INFORMATION ACQUISITION APPARATUS INCLUDING THE SAME

(71) Applicant: CANON KABUSHIKI KAISHA, Tokyo (JP)

(72) Inventors: Yukihiro Inoue, Tucson, AZ (US); Hideo Iwase, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 42 days.

(21) Appl. No.: 14/724,434

(22) Filed: May 28, 2015

(65) Prior Publication Data

US 2015/0354940 A1 Dec. 10, 2015

(30) Foreign Application Priority Data

Jun. 6, 2014 (JP) .................. 2014-118109

(51) Int. Cl.
*G01N 21/00* (2006.01)
*G01B 9/02* (2006.01)
(Continued)

(52) U.S. Cl.
CPC ..... *G01B 9/02091* (2013.01); *G01B 9/02009* (2013.01); *G01B 9/02044* (2013.01); *G01J 3/10* (2013.01); *G01J 3/44* (2013.01); *G01N 21/4795* (2013.01); *G01N 21/65* (2013.01); *G02F 1/3536* (2013.01); *G02F 1/3544* (2013.01); *G02F 1/395* (2013.01); *A61B 5/0033* (2013.01); *A61B 5/0066* (2013.01); *A61B 5/0071* (2013.01); *G01N 2021/653* (2013.01); *G01N 2021/655* (2013.01); *G02B 21/16* (2013.01); *G02F 2001/3528* (2013.01); *G02F 2203/04* (2013.01)

(58) Field of Classification Search
CPC .. G01N 21/65; G01B 9/02; A61B 5/00; A61B 1/06; A61B 1/00; A61B 1/07; A61B 1/04; F21V 8/00
See application file for complete search history.

(56) References Cited

U.S. PATENT DOCUMENTS

2005/0226577 A1* 10/2005 Alfano ................ H04B 10/506
385/122

FOREIGN PATENT DOCUMENTS

| JP | 5-181174 A | 7/1993 |
|---|---|---|
| JP | 2003-156772 A | 5/2003 |
| JP | 2004-93583 A | 3/2004 |

OTHER PUBLICATIONS

R. Andrew Wall, et al., "Fluorescence-based surface magnifying chromoendoscopy and optical coherence tomography endoscope", Journal of Biomedical Optics 17(8), 086003, Aug. 2012, pp. 086003-1-086003-7.

* cited by examiner

*Primary Examiner* — Abdullahi Nur
(74) *Attorney, Agent, or Firm* — Canon USA, Inc. I.P. Division

(57) ABSTRACT

One or more light source apparatuses, one or more information acquisition apparatuses and related method(s) are discussed herein. At least one embodiment of a light source apparatus includes a light source that generates first pulsed light and a nonlinear optical medium that generates second pulsed light having a wavelength different from that of the first pulsed light due to incidence of the first pulsed light. The light source may be configured so that the center wavelength of the first pulsed light is variable across the zero dispersion wavelength of the nonlinear optical medium.

18 Claims, 9 Drawing Sheets

(51) Int. Cl.
*G01N 21/65* (2006.01)
*G01J 3/44* (2006.01)
*G01N 21/47* (2006.01)
*G01J 3/10* (2006.01)
*G02F 1/35* (2006.01)
*G02F 1/39* (2006.01)
*A61B 5/00* (2006.01)
*G02B 21/16* (2006.01)

LIGHT SOURCE APPARATUS AND INFORMATION ACQUISITION APPARATUS INCLUDING THE SAME

BACKGROUND OF THE INVENTION

Field of the Invention

The present disclosure relates to at least one light source apparatus capable of outputting light having a variable spectral bandwidth, at least one information acquisition apparatus including the same and one or more methods for using the same.

Description of the Related Art

There is a known system for acquiring a tomogram of a subject, called optical coherent tomography (OCT). The OCT system is used for inspecting industrial products, medical diagnosis, and so on because it is nondestructive and noninvasive.

A known method of the OCT system is spectral domain (SD)-OCT that emits light having a broad spectral bandwidth to a subject, and divides light interfering in an OCT optical system with a spectroscope to obtain spectral information. With the SD-OCT, the resolution of the tomogram increases as the spectral bandwidth increases, which requires developing a light source apparatus capable of outputting light having a broad spectral bandwidth.

Furthermore, information on substances included in a subject can be obtained by irradiating the subject with light and detecting one of light scattered by the subject, light passing through the subject, and light generated from the subject. For example, fluorescence imaging is known in the field of biotechnology, in which light with a specific wavelength is applied to a subject marked with a fluorescent dye to cause the subject to emit light, and the distribution of biological substances included in the subject is observed. In such fluorescence imaging, the wavelength of illumination light may be matched with a fluorescent dye absorption wavelength. This requires a light source apparatus capable of outputting light having a center wavelength close to a fluorescent dye absorption wavelength and having a narrow spectral bandwidth. Furthermore, various kinds of fluorescent dye having different absorption wavelengths are used depending on the biological substance observed. This requires a light source apparatus capable of outputting light with a variable center wavelength.

R. Andrew Wall et al., "Fluorescence-based surface magnifying chromoendoscopy and optical coherence tomography endoscope", Journal of Biomedical Optics 17(8), 086003, August, 2012 discloses a multi-modality apparatus in which SD-OCT that emits light with a broad spectral bandwidth and fluorescence imaging that emits a narrow spectral bandwidth are combined.

To emit light with a broad spectral bandwidth and light with a narrow spectral bandwidth to a subject, the multi-modality apparatus disclosed in Journal of Biomedical Optics 17(8), 086003, August, 2012 is equipped with a light source apparatus including two optical systems (light source units) having different characteristics and switches between the optical systems for measurement depending on the modality. This disadvantageously increases the size and cost of the apparatus.

SUMMARY OF THE INVENTION

The present disclosure provides at least one light source apparatus capable of outputting light with a broad spectral bandwidth and light with a narrow spectral bandwidth and a variable center wavelength from a single light source apparatus.

At least one light source apparatus according to an aspect of the present disclosure includes a light source that generates first pulsed light and a nonlinear optical medium that generates second pulsed light having a wavelength different from that of the first pulsed light due to incidence of the first pulsed light. The light source apparatus may be configured so that the center wavelength of the first pulsed light is variable across the zero dispersion wavelength of the nonlinear optical medium.

According to other aspects of the present inventions, one or more additional light source apparatuses, one or more information acquisition apparatuses, and methods of operating or using the same are discussed herein. Further features of the present inventions will become apparent from the following description of exemplary embodiments with reference to the attached drawings.

DESCRIPTION OF THE EMBODIMENTS

Figure 1:
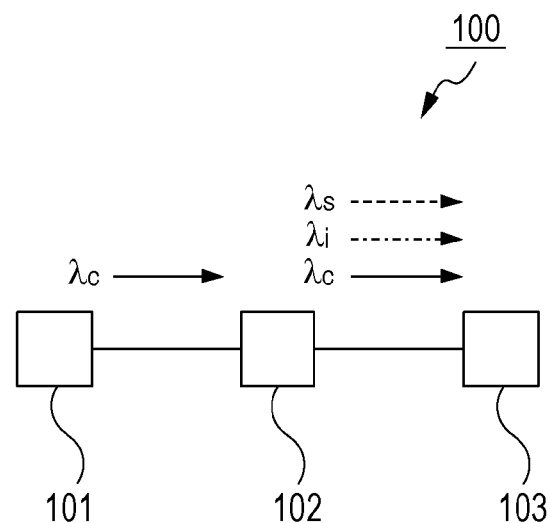
FIG. 1 is a schematic diagram of a configuration example of a light source apparatus according to a first embodiment.

A light source apparatus according to an embodiment of the present disclosure includes an exciting light source that emits excitation light or first pulsed light and a nonlinear optical medium that generates second pulsed light due to the incident first pulsed light. When excitation light enters the nonlinear optical medium, light having a center wavelength different from that of the excitation light is generated by four-wave mixing that occurs in the nonlinear optical medium. A widely used nonlinear optical medium is an optical fiber. In the present disclosure, the center wavelength is a wavelength at the highest peak intensity.

First, the principle of generation of four-wave mixing, which is an important phenomenon in the present disclosure, will be described. The four-wave mixing is one of parametric effects, in which, when two excitation lights with different center wavelengths are introduced into a nonlinear optical medium, such as a fiber, light with a center wavelength different from the above-mentioned wavelengths is newly generated. At that time, part of the energy of the excitation light that has entered the nonlinear optical medium is converted to the energy of the light generated by four-wave mixing. For example, two excitation lights having frequencies (the reciprocals of the center wavelengths) of $\omega_1$ and $\omega_2$, respectively, are introduced into a nonlinear optical medium, two lights having frequencies of $\omega_3$ and $\omega_4$, respectively, are newly generated. The frequencies satisfy the relation $\omega_1 + \omega_2 = \omega_3 + \omega_4$.

If the excitation lights have the same frequency, that is, $\omega_1 = \omega_2 = \omega_c$, two lights having frequencies of $\omega_c + \Delta\omega$ and $\omega_c - \Delta\omega$, respectively, are generated in symmetry about the frequency $\omega_c$, which is called degenerate four-wave mixing. In general, light at higher frequencies (shorter center wavelengths) is called signal light, and light at lower frequencies (longer center wavelengths) is called idler light. In this specification, both of the lights, if not distinguished from each other, are referred to as generated light. The frequency of signal light is hereinafter expressed as $\omega_s$ $(=\omega_c+\Delta\omega)$, and the frequency of idler light is expressed as $\omega_i$ $(=\omega_c-\Delta\omega)$.

The degenerate four-wave mixing is widely used in light source apparatuses for information acquisition apparatuses because control of the wavelength and the system configuration are easier than that of a case in which two lights having different frequencies are introduced. Thus, this application describes a light source apparatus using the degenerate four-wave mixing.

For efficient degenerate four-wave mixing, the following phase matching condition needs to be satisfied:

$$-4\gamma P_c < \Delta\beta = \beta_s + \beta_i - 2\beta_c < 0 \quad \text{Exp. (1)}$$

$$\gamma = \frac{\omega_c}{c} \frac{n_2}{A_{\text{eff}}}$$

where $\beta_c$ is the propagation constant of excitation light in a nonlinear optical medium, $\beta_s$ is the propagation constant of signal light, $\beta_i$ is the propagation constant of idler light, $\Delta\beta$ indicates the phase mismatching of propagation constants of lights in the nonlinear optical medium, $\gamma$ is the nonlinear coefficient of the nonlinear optical medium, $P_c$ is the peak intensity of the excitation light, that is, a peak intensity at the center wavelength, $n_2$ is the nonlinear refractive index of the nonlinear optical medium, $A_{\text{eff}}$ is the effective cross-sectional area of the optical fiber, which is the nonlinear optical medium, and c is the velocity of light in a vacuum.

The phase mismatching $\Delta\beta$ of the propagation constants of lights in the nonlinear optical medium can be expressed by the following expression using the frequency difference $\Delta\omega$:

$$\Delta\beta = \beta_2(\Delta\omega)^2 + \beta_4(\Delta\omega)^4/12 \quad \text{Exp. (2)}$$

where $\beta_2$ is a group velocity dispersion of the nonlinear optical medium at the frequency of the excitation light, and $\beta_4$ is the second derivative of the group velocity dispersion $\beta_2$. The group velocity dispersion $\beta_2$ is the second derivative of the propagation constant $\beta_c$ of the excitation light.

An optical parametric gain G by the four-wave mixing is expressed by the following expression:

$$G = \left| \frac{\sinh\left(\sqrt{1-(1+\Delta\beta/2\gamma P_c)^2} \, \gamma P_c L\right)}{\sqrt{1-(1+\Delta\beta/2\gamma P_c)^2}} \right|^2 \quad \text{Exp. (3)}$$

where L is the length of the nonlinear optical medium.

Next, graphs of Exp. (2) and Exp. (3) for four kinds of nonlinear optical medium in which $\beta_2$ is positive or negative (including 0), and $\beta_4$ is positive (including 0) or negative will be shown in FIGS. 7A to 10B.

Figure 7A:
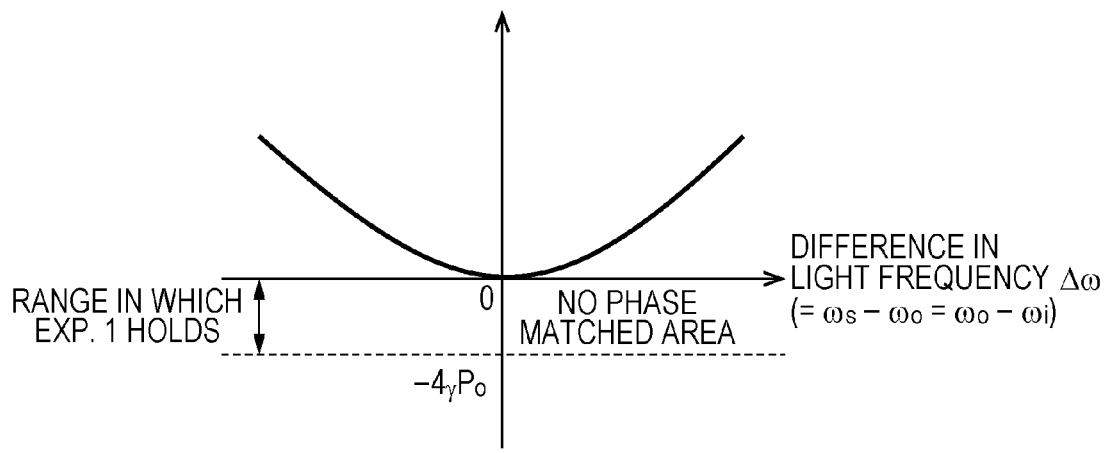
FIGS. 7A to 7B are each a schematic diagram illustrating four-wave mixing generated when a nonlinear optical medium that satisfies $\beta_2>0$ and $\beta_4\geq0$.
Figure 7B:
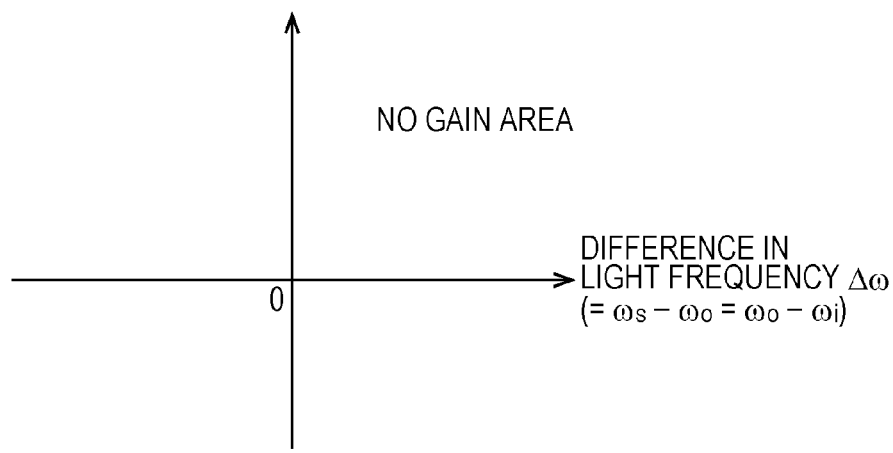

FIGS. 7A and 7B show respectively the phase mismatching $\Delta\beta$ and the optical parametric gain G in the case of a nonlinear optical medium in which $\beta_2 > 0$ and $\beta_4 \geq 0$ hold. FIG. 7A is a graph of Exp. (2), in which the vertical axis indicates $\Delta\beta$, and the horizontal axis indicates $\Delta\omega$. FIG. 7B is a graph of Exp. (3), in which the vertical axis indicates G, and the horizontal axis indicates $\Delta\omega$. This also applies to the graphs in FIGS. 8A to 10B.

Since both the nonlinear coefficient $\gamma$ of the nonlinear optical medium and the peak intensity $P_c$ of the excitation light are positive values, $\Delta\beta$ needs to be a negative value to satisfy Exp. (1). However, if $\beta_2 > 0$ and $\beta_4 \geq 0$, $\Delta\beta$ takes a value equal to or greater than 0, as shown in FIG. 7A, so that a region that satisfies Exp. (1), which is a condition for efficiently generating degenerate four-wave mixing, is not present. That is, $\Delta\omega$ that allows the optical parametric gain G to be obtained is not present, as shown in FIG. 7B. Thus, even if excitation light is introduced into the nonlinear optical medium in which $\beta_2 > 0$ and $\beta_4 \geq 0$ hold, no signal light and no idler light are generated.

Figure 8A:
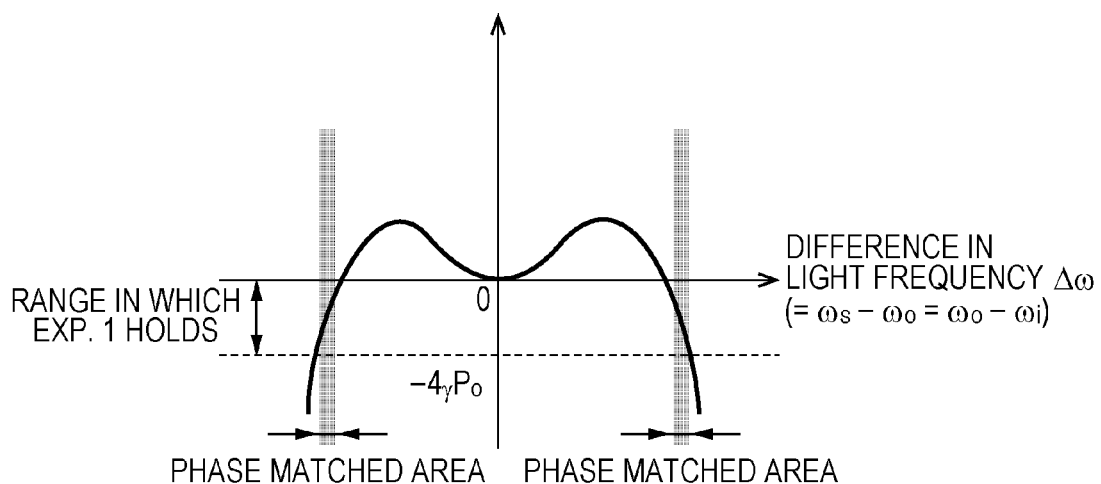
FIGS. 8A to 8B are each a schematic diagram illustrating four-wave mixing generated when a nonlinear optical medium that satisfies $\beta_2>0$ and $\beta_4<0$.
Figure 8B:
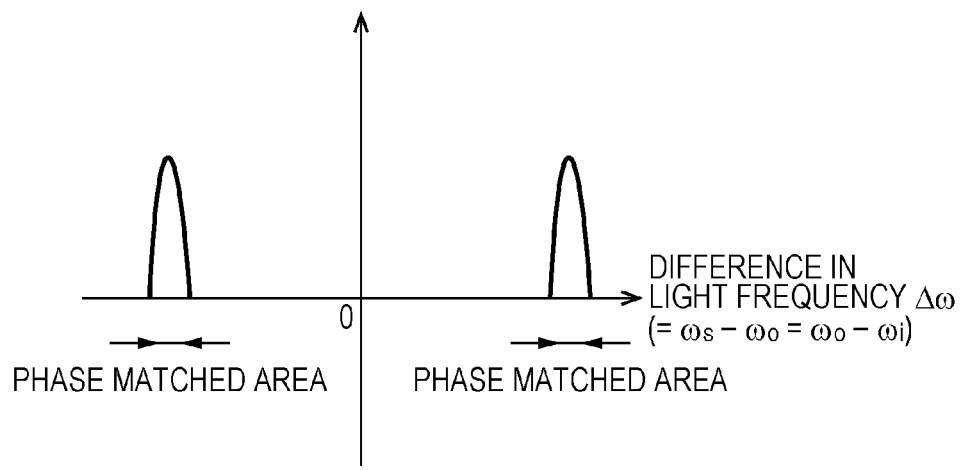

FIGS. 8A and 8B show the case of a nonlinear optical medium in which $\beta_2 > 0$ and $\beta_4 < 0$ hold. In the graph in FIG. 8A, ranges in which the phase matching condition for $\Delta\beta$ expressed by Exp. (1) holds are hatched. The graph shows that the ranges of $\Delta\omega$ that satisfy the phase matching condition expressed by Exp. (1) are each present in a relatively small area apart from the frequency of the excitation light. Accordingly, as shown in FIG. 8B, when excitation light with a given frequency is introduced into the nonlinear optical medium, the optical parametric gain G is present in a relatively narrow frequency band, so that signal light and idler light with a narrow frequency band are generated.

Figure 9A:
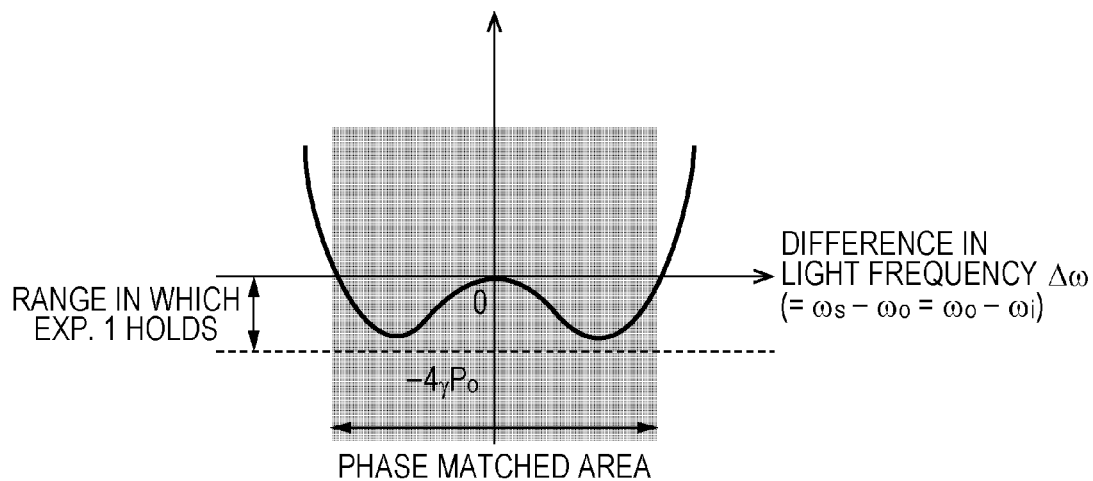
FIGS. 9A to 9B are each a schematic diagram illustrating four-wave mixing generated when a nonlinear optical medium that satisfies $\beta_2\leq0$ and $\beta_4\geq0$.
Figure 9B:
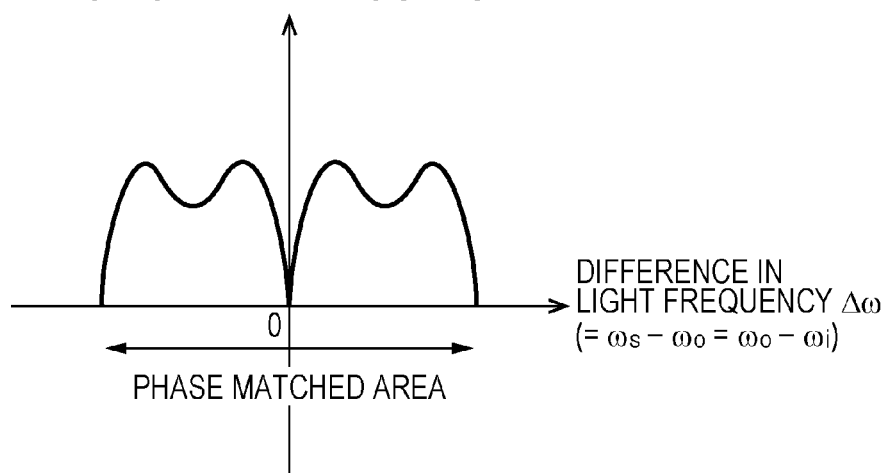
Figure 10A:
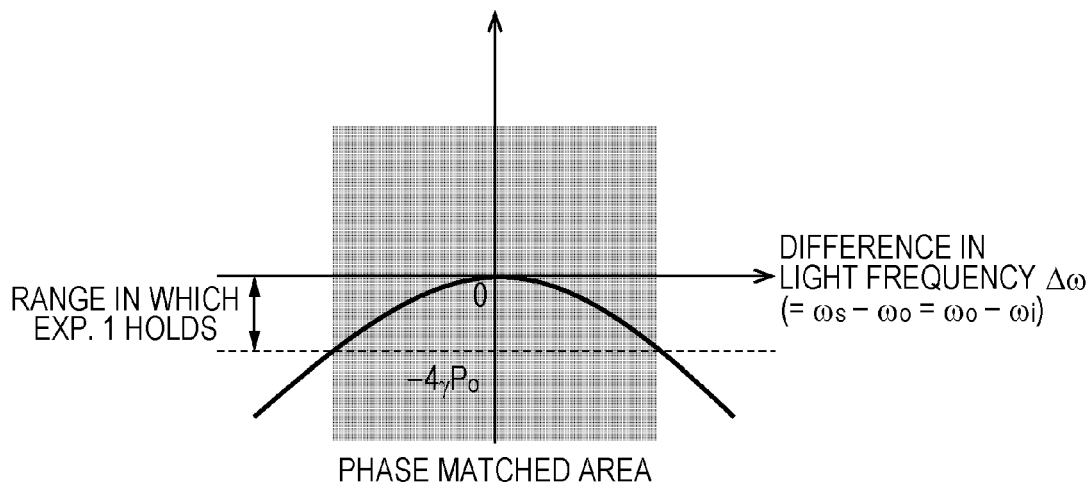
FIGS. 10A to 10B are each a schematic diagram illustrating four-wave mixing generated when a nonlinear optical medium that satisfies $\beta_2\leq0$ and $\beta_4<0$.
Figure 10B:
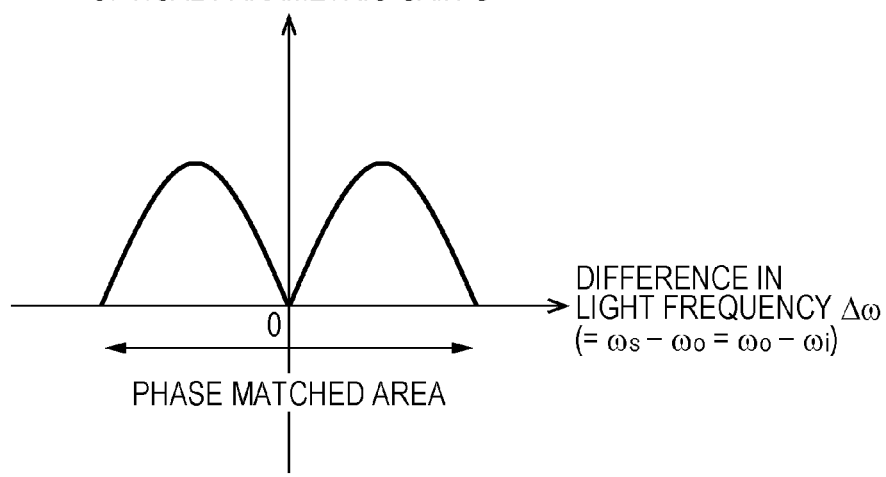

FIGS. 9A and 9B show a nonlinear optical medium in which $\beta_2 \leq 0$ and $\beta_4 \geq 0$ hold, and FIGS. 10A and 10B show a nonlinear optical medium in which $\beta_2 \leq 0$ and $\beta_4 < 0$ hold. FIGS. 9A and 10A show that, in the area of $\beta_2 \leq 0$ (abnormal dispersion area), the range of $\Delta\omega$ (the hatched area) that satisfies the phase matching condition expressed by Exp. (1) expands continuously. That is, since the optical parametric gain G is present in a wide frequency band, signal light and idler light with wide frequency bands are generated, so that light with a wide frequency band, shown in FIGS. 9B and 10B, is obtained.

Thus, to generate light with a narrow spectral bandwidth (narrow band light) using degenerate four-wave mixing, a nonlinear optical medium that satisfies $\beta_2 > 0$ and $\beta_4 < 0$ may be used. To generate pulsed light with a broad spectral bandwidth (broad band light) using degenerate four-wave mixing, a nonlinear optical medium that satisfies $\beta_2 \leq 0$ may be used. In the present disclosure, the light with a narrow spectral bandwidth (narrow band light) is pulsed light with a spectral bandwidth of 10 nm or less, and the light with a broad spectral bandwidth (broad band light) is pulsed light with a spectral bandwidth of 100 nm or more.

Desirable values $\beta_2$ and $\beta_4$ for the nonlinear optical medium can be given by using an optical fiber made of a combination of a core material and a clad material selected to achieve a suitable difference in refractive index between the core and clad of the optical fiber.

If $\beta_2>0$ and $\beta_4<0$, a frequency shift amount $\Delta\omega$ (a wavelength shift amount $\Delta\lambda$) of light generated from excitation light due to degenerate four-wave mixing, and the frequency width $\delta\omega$ (spectral half-width $\delta\lambda$) of the generated light are expressed by the following expressions, respectively:

$$\Delta\omega = \sqrt{\frac{12\beta_2}{|\beta_4|}} = \sqrt{\frac{12\beta_3(\omega_C - \omega_0)}{|\beta_4|}} \quad \text{Exp. (4)}$$

$$\Delta\lambda = \frac{1}{A}\sqrt{\frac{12\beta_2}{|\beta_4|}} = \frac{1}{A}\sqrt{\frac{12\beta_3 A(\lambda_0 - \lambda_C)}{|\beta_4|}} \quad \text{Exp. (5)}$$

$$A = \frac{2\pi c}{\lambda_0^2}$$

$$\delta\omega = \frac{24\gamma P_C}{|\beta_4|\Delta\omega^3} \quad \text{Exp. (6)}$$

$$\delta\lambda = \frac{24\gamma P_C}{A^4|\beta_4|\Delta\lambda^3} \quad \text{Exp. (7)}$$

where $\omega_0$ is the zero-dispersion frequency of the nonlinear optical medium, $\lambda_c$ is the center wavelength of the excitation light, $\lambda_0$ is the zero-dispersion frequency of the nonlinear optical medium, and $\beta_3$ is the first derivative of the group velocity dispersion $\beta_2$ at the zero-dispersion frequency.

Exp. (5) shows that the wavelength shift amount $\Delta\lambda$ increases by the coefficient as compared with a change in the center wavelength $\lambda_c$ of the excitation light. That is, even if the change in the center wavelength $\lambda_c$ of the excitation light is small, the shift amount of the center wavelength of the signal light (or the idler light) is large. Furthermore, Exp. (7) shows that using a nonlinear optical medium in which the nonlinear coefficient $\gamma$ is small and $\beta_4$ is large allows generating signal light (or idler light) with a narrow spectral bandwidth $\delta\lambda$.

This is the principle of generation of four-wave mixing (particularly, degenerate four-wave mixing).

In some embodiments of the present disclosure, light with a narrow spectral bandwidth and a variable center wavelength and light with a broad spectral bandwidth can be output with a single light source apparatus, that is, a single optical system, using the characteristics of degenerate four-wave mixing, described above. In other words, the light source apparatus according to an embodiment of the present disclosure has a first mode in which light with a narrow spectral bandwidth and a variable center wavelength is output and a second mode in which light with a broad spectral bandwidth is output.

Figure 5A:
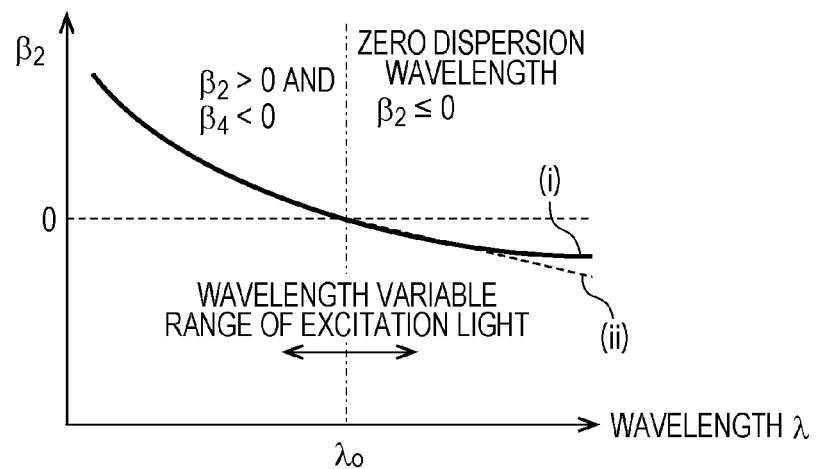
FIGS. 5A to 5C are each a graph showing a relationship between the zero dispersion wavelength of a nonlinear optical medium and the wavelength of excitation light suitable for the present disclosure.

Specifically, the light source apparatus uses excitation light whose center wavelength is variable across the zero dispersion wavelength of a nonlinear optical medium having a group velocity dispersion characteristic (i) or (ii) shown in FIG. 5A. The zero dispersion wavelength of the nonlinear optical medium is a wavelength at which the group-velocity dispersion $\beta_2$ is zero.

Figure 5B:
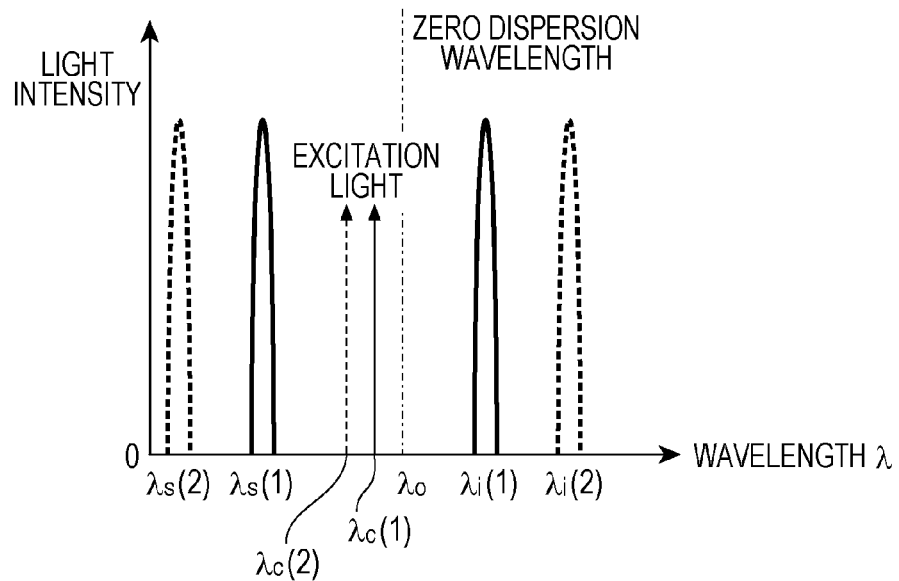
Figure 5C:
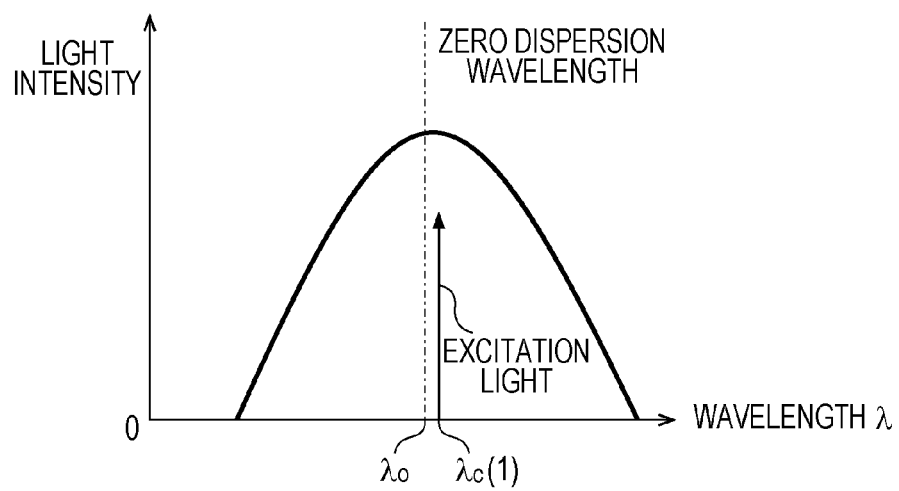

The nonlinear optical medium having the group-velocity dispersion characteristic (i) or (ii) shown in FIG. 5A satisfies $\beta_2>0$ and $\beta_4<0$ on the short wavelength side with respect to the zero dispersion wavelength $\lambda_0$ and satisfies $\beta_2\leq0$ on the long wavelength side with respect to the zero dispersion wavelength $\lambda_0$. When excitation light with a center wavelength $\lambda_c$ shorter than the zero dispersion wavelength $\lambda_0$ of the nonlinear optical medium is introduced into a nonlinear optical medium having the group-velocity dispersion characteristic (i) or (ii), the apparatus goes to the first mode in which idler light having the center wavelength $\lambda_i$ and signal light having the center wavelength $\lambda_s$ are generated, as shown in FIG. 5B. When the center wavelength $\lambda_c$ of the excitation light is changed, the center wavelengths $\lambda_i$ and $\lambda_s$ of the generated light are also changed according to $\lambda_c$. When excitation light having a center wavelength $\lambda_c$ longer than the zero dispersion wavelength $\lambda_0$ of the nonlinear optical medium is introduced, the wavelength bands of the idler light and signal light are added to the spectrum of the excitation light, and the apparatus goes to the second mode in which broad band light having a spectral bandwidth wider than that of the excitation light, as shown in FIG. 5C, is generated.

Figure 6A:
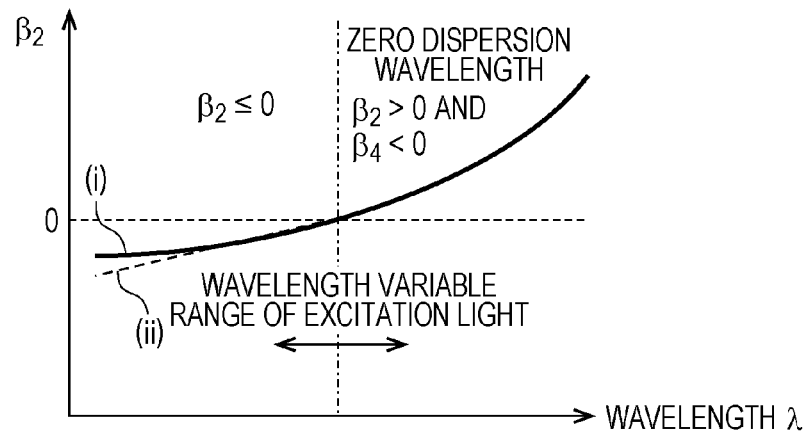
FIGS. 6A to 6C are each a graph showing another relationship between the zero dispersion wavelength of a nonlinear optical medium and the wavelength of excitation light suitable for the present disclosure.
Figure 6B:
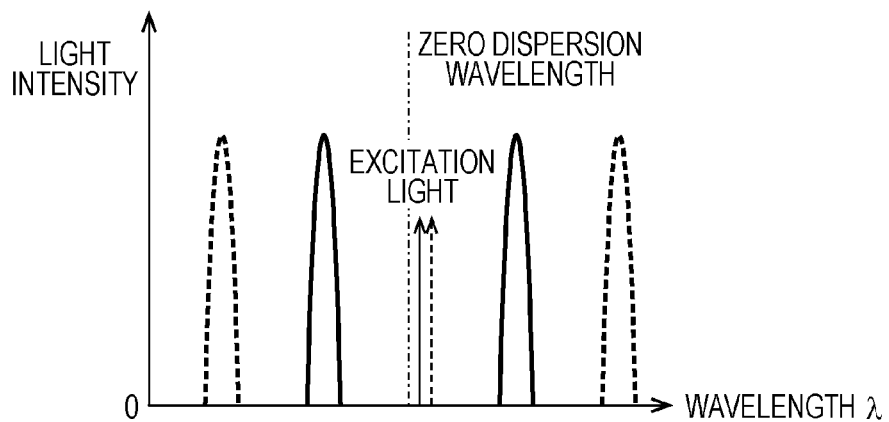
Figure 6C:
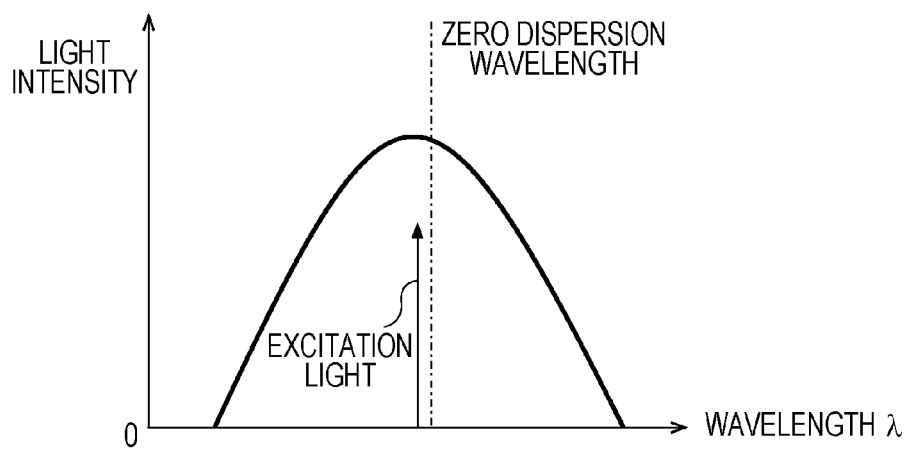

A nonlinear optical medium having a group velocity dispersion characteristic (i) or (ii) shown in FIG. 6A may be used instead of that shown in FIG. 5A. The nonlinear optical medium having the group-velocity dispersion characteristic shown in FIG. 6A satisfies $\beta_2>0$ and $\beta_4<0$, on the long wavelength side with respect to the zero dispersion wavelength $\lambda_0$ and satisfies $\beta_2\leq0$ on the short wavelength side with respect to the zero dispersion wavelength $\lambda_0$. When excitation light having a center wavelength $\lambda_c$ longer than the zero dispersion wavelength $\lambda_0$ of the nonlinear optical medium is introduced into the nonlinear optical medium having this group-velocity dispersion characteristic (i) or (ii), the apparatus goes to the first mode in which two narrow band lights having the center wavelengths $\lambda_i$ and $\lambda_s$, respectively, as shown in FIG. 6B, are generated. When the center wavelength $\lambda_c$ of the excitation light is changed, the center wavelengths $\lambda_i$ and $\lambda_s$ of the pulsed light are also changed according to $\lambda_c$. When excitation light having a center wavelength $\lambda_c$ shorter than the zero dispersion wavelength $\lambda_0$ of the nonlinear optical medium is introduced, the wavelength bands of the idler light and signal light are added to the spectrum of the excitation light, and the apparatus goes to the second mode in which broad band light having a spectral bandwidth wider than that of the excitation light, as shown in FIG. 6C, is generated.

In summary, if the center wavelength of the excitation light is changed opposite to the first mode with respect to the zero dispersion wavelength in the nonlinear optical medium, the apparatus goes to the second mode. The light source apparatus of the present disclosure may use a nonlinear optical medium having a characteristic that satisfies the relation of Exp. (8) or (9). When the center wavelength of the excitation light is changed across the zero dispersion wavelength of the nonlinear optical medium, pulsed light (narrow band light) having a variable center wavelength and broad band light can be output from a single light source apparatus.

If $\lambda_c<\lambda_0$, $\beta_2>0$ and $\beta_4<0$, and if $\lambda_c\geq\lambda_0$, $\beta_2\leq0$     Exp. (8)

If $\lambda_c\leq\lambda_0$, $\beta_2\leq0$, and if $\lambda_c>\lambda_0$, $\beta_2>0$ and $\beta_4<0$     Exp. (9)

Light source apparatuses and information acquisition apparatuses according to some embodiments of the present disclosure will now be described with reference to the drawings. However, the configurations are given for mere illustration and are not intended to limit the present disclosure. In the drawings, components denoted by the same reference signs are the same components or corresponding components. Descriptions of commonalities among the embodiments will be sometimes omitted.

First Embodiment

FIG. 1 is a schematic diagram of a light source apparatus according to a first embodiment. A light source apparatus 100 includes an exciting light source 101 that generates pulsed light or excitation light, a nonlinear optical medium 102 that satisfies the condition of Exp. (8) or (9), and a light output unit 103. The excitation light generated from the exciting light source 101 is introduced into the nonlinear optical medium 102 to generate light with a wavelength different from that of the excitation light, and the generated light is extracted via the light output unit 103.

The exciting light source 101 is a light source capable of emitting pulsed light having a center wavelength that is variable across the zero dispersion wavelength of the nonlinear optical medium 102. The exciting light source 101 may be any light source that emits pulsed light whose center wavelength is variable, for example, a known light source equipped with an etalon filter or a spectral grating.

The nonlinear optical medium 102 may be an optical fiber having a high nonlinear coefficient, specifically, a photonic crystal fiber and a tapered fiber.

The photonic crystal fiber is a fiber having many air holes in the clad of the optical fiber. The air holes allow the refractive index of the clad to be extremely lower than that of the core. This can decrease an effective core diameter (a mode field diameter), thus offering a great nonlinear effect even with a fiber length of a few meters. Adjusting the size and pitch of the air holes can offer any wavelength dispersion characteristic.

The tapered fiber is an optical fiber having a small clad diameter, which can be manufactured by heating and drawing a general optical fiber. A tapered fiber having an extremely small clad diameter of a few micrometers can offer a great nonlinear effect even with a fiber length of a few millimeters. Adjusting the clad diameter and length of the tapered fiber can offer any desired wavelength dispersion characteristic.

The light source apparatus 100 including the nonlinear optical medium 102 that satisfies Exp. (8) will be described hereinbelow.

When the light source apparatus 100 is operated in the first mode in which pulsed light (narrow band light) having a variable center wavelength is output, excitation light having a center wavelength $\lambda_c$ shorter than the zero dispersion wavelength $\lambda_0$ of the nonlinear optical medium 102 is emitted from the exciting light source 101. Upon receiving the exciting pulsed light, the nonlinear optical medium 102 can generate pulsed light (narrow band light) having a narrow spectral bandwidth. When the center wavelength of the excitation light is changed, the wavelength of generated light can be changed by an amount corresponding to the coefficient in Exp. (5).

The light output unit 103 may include a band-pass filter that rejects light in a wavelength band other than that of output light. Light in an unnecessary wavelength band is rejected by the band-pass filter as needed, and one or two pulsed lights of the excitation light emitted from the exciting light source 101 and idler light and signal light generated in the light source apparatus 100 are output. If the light output unit 103 does not include the band-pass filter, light in an unnecessary wavelength band may be rejected after being output from the light output unit 103.

When the light source apparatus 100 is operated in the second mode for outputting broad band light, light having a center wavelength $\lambda_c$ longer than the zero dispersion wavelength $\lambda_0$ of the nonlinear optical medium 102 is emitted from the exciting light source 101, so that the nonlinear optical medium 102 can generate broad band light.

The excitation light emitted from the exciting light source 101 is preferably pulsed light having a spectral bandwidth of 1 nm or less and, more preferably, 0.1 nm or less. This is because the narrower the spectral bandwidth of the excitation light is, the more efficiently four-wave mixing occurs in the nonlinear optical medium 102, which ensures a sufficient optical parametric gain.

Thus, the combination of a nonlinear optical medium having the dispersion characteristic shown in FIG. 5A and an exciting light source that emits light having a center wavelength that is variable across the zero dispersion wavelength of the nonlinear optical medium allows narrow band light having a variable center wavelength and broad band light to be generated with a single optical system. This allows a compact, low-cost configuration of the light source apparatus.

Second Embodiment

Figure 2:
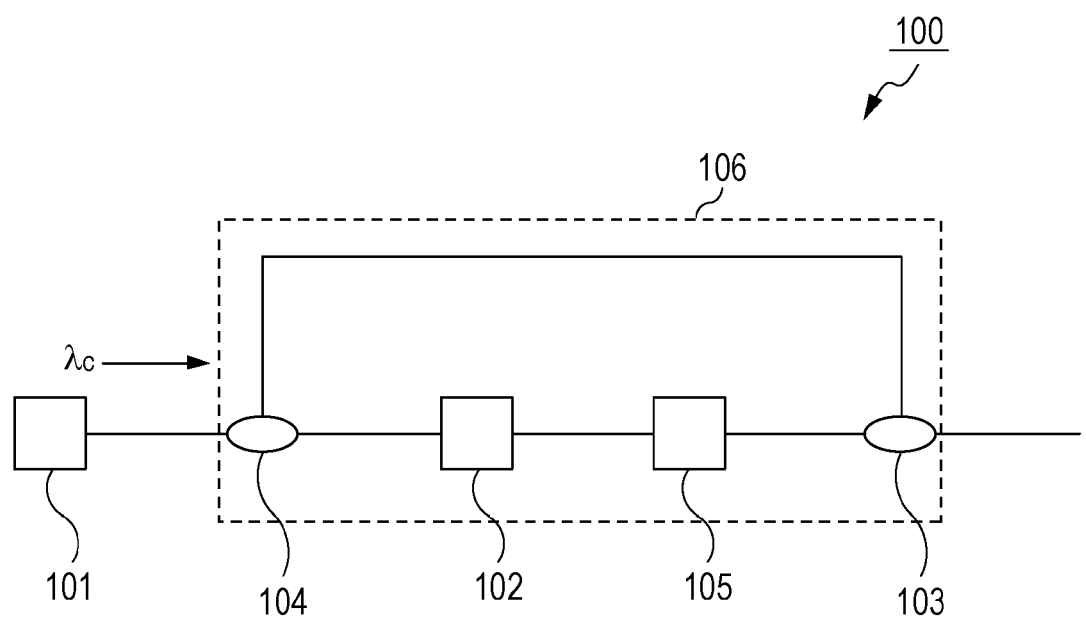
FIG. 2 is a schematic diagram of a configuration example of a light source apparatus according to a second embodiment.

FIG. 2 shows a configuration example of a light source apparatus according to a second embodiment. The light source apparatus 100 includes an exciting light source 101 that generates pulsed light, an optical multiplexer 104, a nonlinear optical medium 102, a band-pass filter 105, and a light extraction coupler (a light output unit) 103.

This embodiment differs from the first embodiment in that the nonlinear optical medium 102 is disposed in an optical resonator 106, with which light generated in the nonlinear optical medium 102 is passed through the nonlinear optical medium 102 a plurality of times to cause parametric oscillation. The optical resonator 106 including the nonlinear optical medium 102 is called a fiber optical parametric oscillator (hereinafter, abbreviated as an FOPO).

The light source apparatus 100 of this embodiment can also use the nonlinear optical medium 102 that satisfies Exp. (8) or (9), as in the first embodiment. Here, a case in which a nonlinear optical medium 102 that satisfies Exp. (8) is used will be described.

In the first mode in which the center wavelength $\lambda_c$ of the excitation light is shorter than the zero dispersion wavelength $\lambda_0$ of the nonlinear optical medium 102, the excitation light emitted from the exciting light source 101 enters the optical resonator 106 through the optical multiplexer 104. While the excitation light propagates in the nonlinear optical medium 102, two pulsed lights having center wavelengths $\lambda_i$ and $\lambda_s$ are generated and circulates in the optical resonator 106 to oscillate. Of the excitation light and the two oscillating pulsed lights, light in an unnecessary wavelength band is rejected by the band-pass filter, and the remaining light is output outside the optical resonator 106 through the light extraction coupler 103.

To ensure a sufficient optical parametric gain in the nonlinear optical medium 102, the excitation light is preferably pulsed light having a spectral bandwidth of 1 nm or less and, more preferably, 0.1 nm or less. The pulse rate of the excitation light is preferably set to an integral multiple of the free spectral range (hereinafter, sometimes abbreviated as FSR) of the optical resonator 106 at the wavelength of output pulsed light of the idler light and signal light. This allows the generated light to be efficiently oscillated in the optical resonator 106 and be output as pulsed light having high peak intensity.

In the second mode in which the center wavelength $\lambda_c$ of the excitation light emitted from the exciting light source 101 is longer than the zero dispersion wavelength $\lambda_0$ of the nonlinear optical medium 102, broad band light having a broad spectral bandwidth is generated while the excitation light propagates in the nonlinear optical medium 102 and is output.

This embodiment allows pulsed light having high peak intensity to be extracted using the nonlinear optical medium 102 provided in the optical resonator 106 in addition to the advantages of the first embodiment.

Third Embodiment

In this embodiment, a multi-modality apparatus in which a first measurement system for stimulated Raman scattering (SRS) imaging and a second measurement system for SD-OCT are combined will be described as an information acquisition apparatus including a light source apparatus according to an embodiment of the present disclosure.

The SRS imaging is a technique for molecule vibrational imaging using the phenomenon of stimulated Raman scattering in which Stokes light is amplified due to the interference between pump light and Stokes light applied to a substance. Specifically, one (Stokes light) of two pulsed lights having different wavelengths is modulated in intensity to synchronize the two pulsed lights, and the synchronized light is applied to the subject. When the difference frequency between the two wavelengths matches the molecular frequency of molecules that compose the subject, stimulated Raman scattering occurs to amplify the pulsed light (Stokes light) whose intensity is modulated. At that time, the pulsed light (pump light) whose intensity is not modulated is attenuated in accordance with the modulation of the intensity of the Stokes light. Thus, by detecting the modulation of the intensity of the pump light that has passed through the subject due to stimulated Raman scattering, molecule vibration imaging of the subject can be performed. Furthermore, by changing the center wavelengths of the pulsed light to change the difference frequency between the two wavelengths, the difference frequency can be matched with the molecular frequencies of various molecules, so that signals unique to a group of molecules that compose the subject can be obtained.

Figure 3:
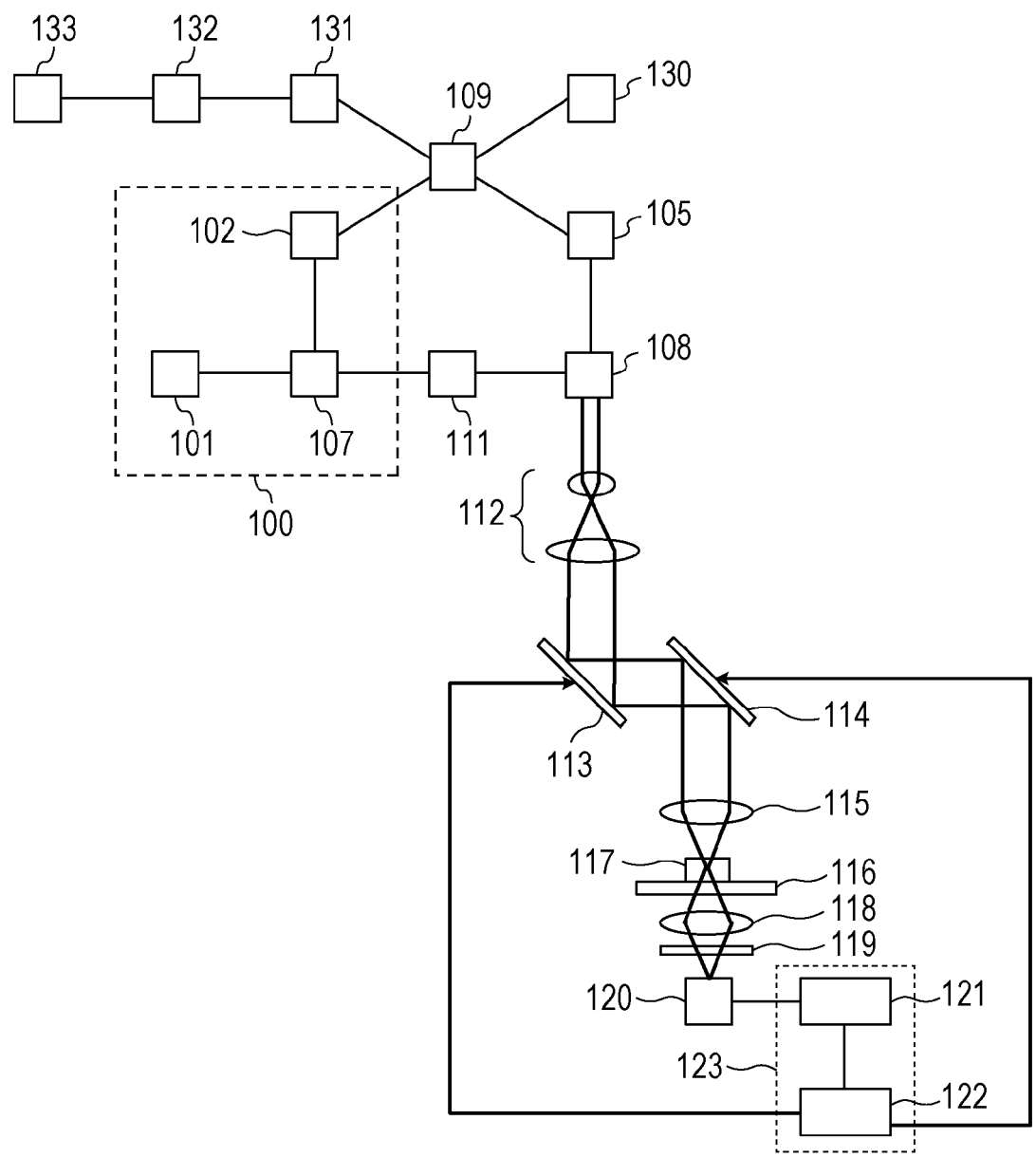
FIG. 3 is a schematic diagram of a configuration example of an information acquisition apparatus including an SRS microscope and an SD-OCT system using a light source apparatus according to an embodiment.

FIG. 3 is a schematic diagram of the multi-modality apparatus in which an SD-OCT and a microscope for SRS imaging (an SRS microscope) are combined.

First, a first measurement system for operating the multi-modality apparatus of this embodiment as an SRS microscope will be described. The first measurement system for the SRS microscope divides excitation light emitted from the exciting light source 101 with an optical divider 107, and modulates one of the divided lights with an optical modulator 111 for use as Stokes light for the SRS microscope. The other light is introduced into the nonlinear optical medium 102 to generate signal light and idler light. One of the lights (in this embodiment, signal light) is extracted via an optical divider 109 and the band-pass filter 105 for use as pump light for the SRS microscope. Setting the center wavelength of the excitation light emitted from the exciting light source 101 shorter than the zero dispersion wavelength of the nonlinear optical medium 102 allows the signal light and the idler light to be generated as narrow band light having a narrow spectral bandwidth.

The Stokes light and the pump light for the SRS microscope are multiplexed by an optical multiplexer 108. Examples of the optical multiplexer 108 include an optical coupler, a diffraction grating, and a prism.

The Stokes light and the pump light multiplexed by the optical multiplexer 108 pass through a beam expander 112, an X-scanning mirror 113, an Y-scanning mirror 114, and an objective lens 115 and are focused on a subject 117 placed on a stage 116. At the focal point, stimulated Raman scattering occurs due to the interference between the pump light and the Stokes light. The pump light modulated in intensity by the stimulated Raman scattering is incident on a light receiving element 120 via a focusing lens 118 and a band-pass filter 119.

Since the Raman scattering cross-sectional area a of molecules is generally small, a change in the intensity of the pump light due to the stimulated Raman scattering is also very small. Thus, SRS signals detected from the change in the intensity of the pump light are sometimes buried in noise. This embodiment performs molecule vibration imaging of the subject 117 by detecting a change in the intensity of the pump light, which is received by the light receiving element 120 and converted into electrical signals, in synchronism with the modulation frequency of the optical modulator 111 using an information acquisition unit 123 including a synchronous detector 121 and a control unit 122. Amplifying the detected synchronizing signals allows high-sensitive detection of SRS signals.

Examples of the synchronous detector 121 include a lock-in amplifier and an FFT analyzer. The FFT analyzer can detect SRS signals at higher speed than the lock-in amplifier. Although FIG. 3 shows a configuration in which the synchronous detector 121 and the control unit 122 are separate from each other, the information acquisition unit 123 may have a configuration in which the synchronous detector 121 and the control unit 122 are combined. An example of the configuration in which the synchronous detector 121 and the control unit 122 are combined is a computer including a CPU serving as the control unit 122 incorporates an application having a synchronism detecting function.

Scanning the focal point on the subject 117 using the X-scan mirror 113 and the Y-scanning mirror 114 forms a two-dimensional image.

If the center wavelength $\lambda_c$ of the excitation light is changed on the short wavelength side with respect to the zero dispersion wavelength $\lambda_0$ of the nonlinear optical medium 102, the center wavelength of the signal light (pump light for the SRS microscope) changes. That is, the difference frequency between the excitation light (Stokes light for the SRS microscope) and the signal light (pump light for the SRS microscope) changes. This allows the difference frequency to be matched with the molecular frequencies of the plurality of kinds of molecules, thus allowing molecule vibration imaging of the plurality of kinds of molecules that compose the subject.

Next, a second measurement system for operating the multi-modality apparatus of this embodiment as an SD-OCT system will be described.

Excitation light having a center wavelength longer than the zero dispersion wavelength of the nonlinear optical medium 102 is emitted from the exciting light source 101 into the nonlinear optical medium 102 to generate broad band light. Since broad band light for use in SD-OCT may be in a fixed wavelength band, there is no need to change the wavelength of the excitation light for scanning.

The generated broad band light is divided into two, measurement light and reference light, by the optical divider 109. The measurement light is output via the band-pass filter 105, the optical multiplexer 108 and irradiates the subject 117 placed on the stage 116 via the beam expander 112, the X-scan mirror 113, the Y-scanning mirror 114, and the objective lens 115. Light reflected by the subject 117 returns to the optical divider 109 through the same path as that of the measurement light.

The reference light is incident on the reference mirror 130 and is reflected by the reference mirror 130 back to the optical divider 109. The reference light reflected by the reference mirror 130 and the measurement light reflected by the subject 117 interfere with each other at the optical divider 109. The interfering light is spectrally divided by a spectroscope 131 and is detected as light spectral information by a detector (a line sensor) 132. The light spectral information detected by the line sensor 132 is processed, such as Fourier-transformed, by an information acquisition unit 133 into tomographic information. Scanning an irradiated point on the subject 117 with the X-scan mirror 113 and the Y-scanning mirror 114 allows two-dimensional tomographic information to be obtained.

The excitation light emitted from the exciting light source 101 of this embodiment is preferably pulsed light with a pulse width of 1 ns or less and, more preferably, 100 ps or less. This is because the peak intensity of the pulsed light can be increased as the pulse width of the pulsed light decreases, thus allowing accurate detection of a nonlinear effect generated in the subject 117.

The pulse rate of the excitation light emitted from the exciting light source 101 is preferably 1 MHz or more and 1 GHz or less. This is because 1 MHz or more is preferable to achieve a practical measuring speed for the multi-modality apparatus, and 1 GHz or less is preferable to prevent a thermal break of the subject 117.

The spectral bandwidth of the excitation light emitted from the exciting light source 101 is preferably 1 nm or less and, more preferably, 0.1 nm or less. This is because the smaller the spectral bandwidth of the pulsed light is, the more efficiently four-wave mixing occurs in the nonlinear optical medium 102, thus ensuring a sufficient optical parametric gain.

Since the multi-modality apparatus according to this embodiment is suitable for observation of biological tissue, the excitation light emitted from the exciting light source 101 may have a wavelength at which the light is hardly reflected, absorbed, and scattered and is easily transmitted by biological tissue. Accordingly, the center wavelength of the excitation light emitted from the exciting light source 101 is preferably 300 nm or more and 1,500 nm or less and, more preferably, 700 nm or more and 1,300 nm or less.

An information acquisition apparatus that applies pulsed light to the subject 117 to detect coherent anti-Stokes Raman scattering generated in the subject 117 and an information acquisition apparatus that detects fluorescence generated in the subject 117 may have the same configuration as that of this embodiment.

Using the multi-modality apparatus in which the light source apparatus according to an embodiment of the present disclosure is combined with an SD-OCT system and an SRS microscope allows light having a broad spectral bandwidth and light having a narrow spectral bandwidth and a variable center wavelength to be output from a single light source. T This allows a compact, low-cost configuration of the light source apparatus. In this embodiment, a microscope has been described as an example, whereas this is applicable to an endoscope apparatus.

This embodiment uses a nonlinear optical medium that satisfies $\beta_2 > 0$ and $\beta_4 < 0$ on the short wavelength side with respect to the zero dispersion wavelength $\lambda_0$, and satisfies $\beta_2 \leq 0$ on the long wavelength side with respect to the zero dispersion wavelength $\lambda_0$, where $\lambda_0$ is the zero dispersion wavelength of the nonlinear optical medium, $\lambda_c$ is the center wavelength of the first pulsed light, $\beta_2$ is the group velocity dispersion of the nonlinear optical medium at the center wavelength $\lambda_c$, and $\beta_4$ is the second derivative of the group velocity dispersion $\beta_2$. With this configuration, when subject information is to be obtained using the first measurement system that constitutes the SRS microscope, the center wavelength of the first pulsed light is set shorter than the zero dispersion wavelength $\lambda_0$, and when subject tomographic information is to be obtained using the second measurement system, which is an SD-OCT system, the center wavelength of the first pulsed light is set longer than the zero dispersion wavelength $\lambda_0$. Alternatively, a nonlinear optical medium that satisfies $\beta_2 > 0$ and $\beta_4 < 0$ on the long wavelength side with respect to the zero dispersion wavelength $\lambda_0$, and satisfies $\beta_2 \leq 0$ on the short wavelength side with respect to the zero dispersion wavelength $\lambda_0$, where $\lambda_0$ is the zero dispersion wavelength of the nonlinear optical medium, $\lambda_c$ is the center wavelength of the first pulsed light, $\beta_2$ is the group velocity dispersion of the nonlinear optical medium at the center wavelength $\lambda_c$, and $\beta_4$ is the second derivative of the group velocity dispersion $\beta_2$. In this case, when subject information is to be obtained using the first measurement system that constitutes the SRS microscope, the center wavelength of the first pulsed light is set longer than the zero dispersion wavelength $\lambda_0$, and when subject tomographic information is to be obtained using the second measurement system, which is an SD-OCT system, the center wavelength of the first pulsed light is set shorter than the zero dispersion wavelength $\lambda_0$.

Fourth Embodiment

A multi-modality apparatus according to a fourth embodiment of the present disclosure using the light source apparatus 100 according to the first embodiment will be described. The multi-modality apparatus is a combination of a first measurement system, which is a two-photon-excited fluorescence microscope, and a second measurement system, which is an SD-OCT system.

Figure 4:
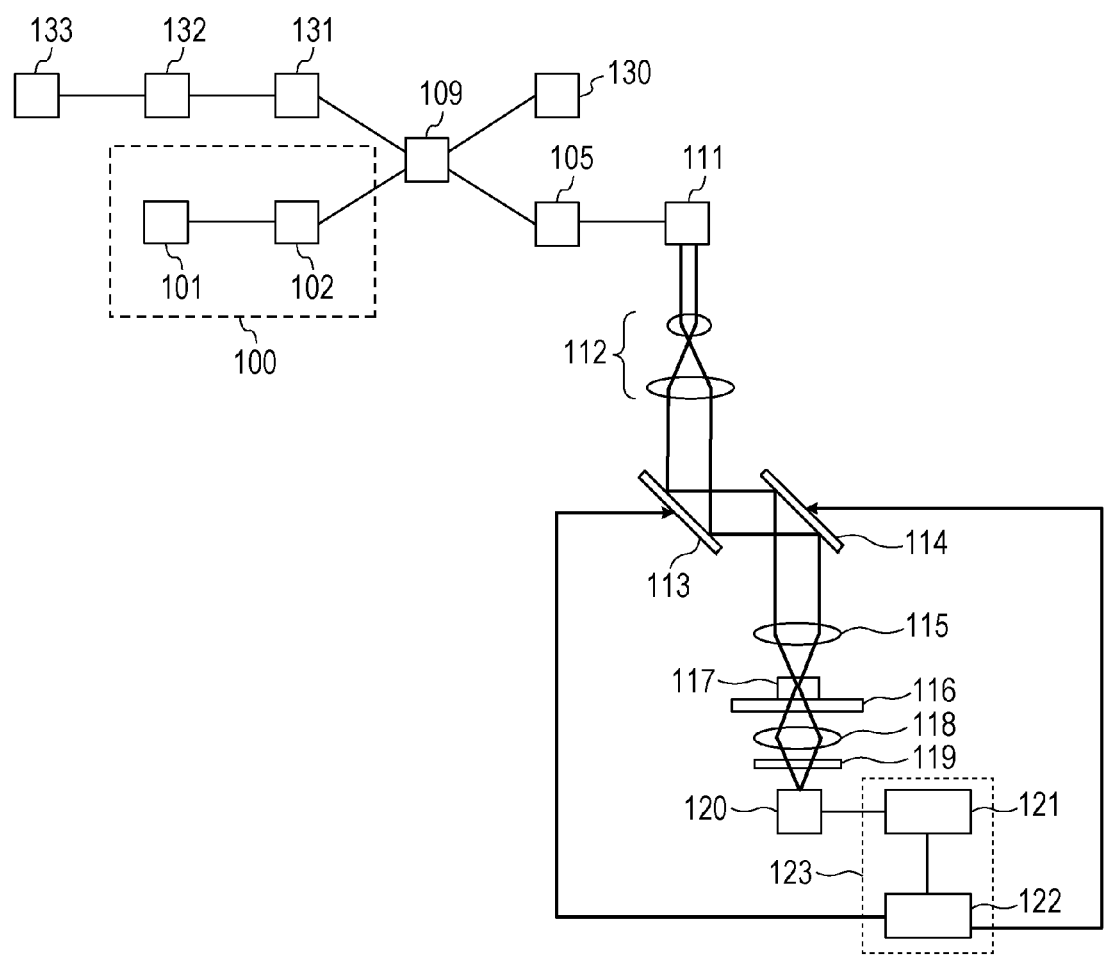
FIG. 4 is a schematic diagram of a configuration example of an information acquisition apparatus including a fluorescence microscope and an SD-OCT system using a light source apparatus according to an embodiment.

FIG. 4 is a schematic diagram of the multi-modality apparatus according to this embodiment. The multi-modality apparatus includes a light source apparatus 100 including an exciting light source 101 and a nonlinear optical medium 102, the first measurement system and the second measurement system. The first measurement system or the two-photon-excited fluorescence microscope includes an optical divider 109, a band-pass filter 105, and an optical modulator 111. The first measurement system further includes a beam expander 112, an X-scan mirror 113, a Y-scanning mirror 114, an objective lens 115, a stage 116, a focusing lens 118, a band-pass filter 119, a light receiving element 120, and an information acquisition unit 123. In the second measurement system or the SD-OCT, a biological cell sample is placed on the stage 115 as the subject 117 to be observed. The second measurement system further includes a reference mirror 130, an optical divider 109, a spectroscope 131, a detector (a line sensor) 132, and an information acquisition unit 133.

First, the first measurement system or the two-photon-excited fluorescence microscope will be described. Excitation light emitted from the exciting light source 101 is introduced into the nonlinear optical medium 102. The wavelength of the excitation light is set shorter than the zero dispersion wavelength of the nonlinear optical medium 102. This allows light with a narrow spectral bandwidth to be generated.

The light generated in the nonlinear optical medium 102 is introduced into the optical modulator 111 through the band-pass filter 105. An example of the band-pass filter 105 is a filter having the characteristics of allowing the wavelength band of the signal light to pass through and blocking light with the other wavelength band.

The light output via the optical modulator 111 is used as excitation light for causing two-photon absorption in the subject 117. The light output from the optical modulator 111 is converted to a beam with a large diameter by the beam expander 112, passes through the X-scan mirror 113 and the Y-scanning mirror 114, and is focused in the subject 117 on the stage 116 by the objective lens 115.

An example of the subject 117 is a biological cell sample marked with a fluorescent dye depending on the kind of the substance to be observed. Fluorescent dyes having different exciting wavelengths are used depending on the biological cell to be marked.

In a minute region of the subject 117 at the center of the focal point of the objective lens 115, the fluorescent dye is two-photon excited to generate fluorescence depending on the exciting wavelength of the fluorescent dye. However, since the two-photon excitation does not occur off the minute region at the center of the focal point, no fluorescence is generated. The spot size of light applied to the subject 117 decreases with an increase in the NA of the objective lens 115, and the size of the minute region in which fluorescence is generated is also decreased.

The two-photon-excited fluorescence generated in the minute region at the center of the focal point is incident on the light receiving element 120 through the focusing lens 118 and the band-pass filter 119 and is acquired as an image signal by the information acquisition unit 123 including a synchronous detector 121 and a control unit 122. The band-pass filter 119 has the characteristic of allowing light with the wavelength band of the target fluorescence to pass through but rejecting light with the other wavelength bands to prevent unnecessary light from entering the light receiving element 120.

An example of the X-scan mirror 113 and the Y-scanning mirror 114 includes a pair of galvanometer mirrors. The X-scan mirror 113 is used for main scanning, and the Y-scanning mirror 114 is used for sub-scanning, which are disposed so that their axes of rotation intersect at right angles. Driving the X-scan mirror 113 and the Y-scanning mirror 114 using the control unit 122 allows two-dimensional scanning of the focal point in the subject 117. After completion of the first two-dimensional scanning, the stage 116 is moved to move the focal point along the optical axis by a predetermined distance, and the same two-dimensional scanning is repeated, so that a three-dimensional image of the subject 117 can be acquired. The control unit 122 may be a store-bought personal computer.

The fluorescence received by the light receiving element 120 and converted to electrical signals is detected in synchronism with the modulating frequency of the optical modulator 111, thus allowing the fluorescence imaging of the subject 117. Amplifying the detected synchronizing signals allows high-sensitive detection of signals.

Examples of the synchronous detector 121 include a lock-in amplifier and an FFT analyzer. The FFT analyzer can detect signals at higher speed than the lock-in amplifier. Although FIG. 4 shows a configuration in which the synchronous detector 121 and the control unit 122 are separate from each other, the information acquisition unit 123 may have a configuration in which the synchronous detector 121 and the control unit 122 are combined. An example of the configuration in which the synchronous detector 121 and the control unit 122 are combined is a computer including a CPU serving as the control unit 122 incorporates an application having a synchronism detecting function.

Next, a case where the SD-OCT or the second measurement system is operated will be described.

Excitation light having a center wavelength longer than the zero dispersion wavelength of the nonlinear optical medium 102 is emitted from the exciting light source 101 into the nonlinear optical medium 102 to generate broad band light. Since broad band light for use in SD-OCT may be in a fixed wavelength band, there is no need to change the wavelength of the excitation light for scanning.

The generated broad band light is divided into two, measurement light and reference light, by the optical divider 109. The measurement light passes through the band-pass filter 105, the beam expander 112, the X-scan mirror 113, the Y-scanning mirror 114, and the objective lens 115 and is applied to the subject 117 placed on the stage 116. Light reflected by the subject 117 returns to the optical divider 109 through the same path as that of the measurement light.

The reference light is incident on the reference mirror 130 and is reflected by the reference mirror 130 back to the optical divider 109. The reference light reflected by the reference mirror 130 and the measurement light reflected by the subject 117 interfere with each other at the optical divider 109. The interfering light is spectrally divided by the spectroscope 131 and is detected as light spectral information by the line sensor 132.

The light spectral information detected by the line sensor 132 is processed, such as Fourier-transformed, by the information acquisition unit 133 into tomographic information. Scanning an irradiated point on the subject 117 with the X-scan mirror 113 and the Y-scanning mirror 114, like the two-photon microscope, allows two-dimensional tomographic information to be obtained.

Since the light source apparatus according to an embodiment of the present disclosure can generate light having a broad spectral bandwidth and light having a narrow spectral bandwidth and a variable center wavelength with a single optical system, the size and cost can be reduced.

While the present inventions have been described with reference to exemplary embodiments, it is to be understood that the inventions are not limited to the disclosed exemplary embodiments. The scope of the following claims is to be accorded the broadest interpretation so as to encompass all such modifications and equivalent structures and functions.

This application claims the benefit of Japanese Patent Application No. 2014-118109, filed Jun. 6, 2014, which is hereby incorporated by reference herein in its entirety.

What is claimed is:
1. A light source apparatus comprising:
a light source that generates first pulsed light; and
a nonlinear optical medium that generates second pulsed light having a wavelength different from a wavelength of the first pulsed light due to incidence of the first pulsed light,
wherein the light source is configured to be capable of emitting, as the first pulsed light, pulsed light having a wavelength shorter than a zero dispersion wavelength of the nonlinear optical medium and pulsed light hav- ing a wavelength longer than the zero dispersion wavelength of the nonlinear optical medium in a switchable manner.

2. The light source apparatus according to claim 1, comprising:
a first mode in which light having a spectral bandwidth of nm or less is output, with a center wavelength of the first pulsed light being longer or shorter than the zero dispersion wavelength of the nonlinear optical medium; and
a second mode in which light having a spectral bandwidth of 100 nm or more is output, with the center wavelength of the first pulsed light being opposite to the zero dispersion wavelength of the nonlinear optical medium in the first mode.

3. The light source apparatus according to claim 1, wherein the nonlinear optical medium satisfies following relations:

when $\lambda_c < \lambda_0$, then $\beta_2 > 0$ and $\beta_4 < 0$; and/or when $\lambda_c \geq \lambda_0$, then $\beta_2 \leq 0$, where $\lambda_0$ is the zero dispersion wavelength of the nonlinear optical medium, $\lambda_c$ is a center wavelength of the first pulsed light, $\beta_2$ is a group velocity dispersion of the nonlinear optical medium at the center wavelength $\lambda_c$, and $\beta_4$ is a second derivative of the group velocity dispersion $\beta_2$.

4. The light source apparatus according to claim 1, further comprising:
a resonator including the nonlinear optical medium and operating to oscillate the second pulsed light,
wherein the first pulsed light has a pulse rate of an integral multiple of a free spectral range of the resonator at a center wavelength of the second pulsed light.

5. The light source apparatus according to claim 1, wherein the nonlinear optical medium includes a photonic crystal fiber or a tapered fiber.

6. The light source apparatus according to claim 1, wherein the first pulsed light and the second pulsed light have a pulse width of 1 ns or less.

7. The light source apparatus according to claim 1, wherein the first pulsed light has a spectral bandwidth of 1 nm or less.

8. The light source apparatus according to claim 1, wherein the nonlinear optical medium satisfies following relations:

when $\lambda_c < \lambda_0$, then $\beta_2 > 0$ and $\beta_4 < 0$; and/or when $\lambda_c \geq \lambda_0$, then $\beta_2 \leq 0$, where $\lambda_0$ is the zero dispersion wavelength of the nonlinear optical medium, $\lambda_c$ is a center wavelength of the first pulsed light, $\beta_2$ is a group velocity dispersion of the nonlinear optical medium at the center wavelength $\lambda_c$, and $\beta_4$ is a second derivative of the group velocity dispersion $\beta_2$.

9. The light source apparatus according to claim 1, wherein the nonlinear optical medium satisfies following relations:

$\beta_2 > 0$ and $\beta_4 < 0$ on a short wavelength side with respect to $\lambda_0$; and $\beta_2 \leq 0$ on a long wavelength side with respect to $\lambda_0$, where $\lambda_0$ is the zero dispersion wavelength of the nonlinear optical medium, $\lambda_c$ is a center wavelength of the first pulsed light, $\beta_2$ is a group velocity dispersion of the nonlinear optical medium at the center wavelength $\lambda_c$, and $\beta_4$ is a second derivative of the group velocity dispersion $\beta_2$.

10. The light source apparatus according to claim 1, wherein the nonlinear optical medium satisfies following relations:

$\beta_2 > 0$ and $\beta_4 < 0$ on a long wavelength side with respect to $\lambda_0$; and $\beta_2 \leq 0$ on a short wavelength side with respect to $\lambda_0$, where $\lambda_0$ is the zero dispersion wavelength of the nonlinear optical medium, $\lambda_c$ is a center wavelength of the first pulsed light, $\beta_2$ is a group velocity dispersion of the nonlinear optical medium at the center wavelength $\lambda_c$, and $\beta_4$ is a second derivative of the group velocity dispersion $\beta_2$.

11. An information acquisition apparatus comprising:
a light source apparatus;
a first measurement system including an information acquisition unit that irradiates a subject with light output from the light source apparatus and detects light reflected from, scattered by, or passing through the subject or light generated in the subject to obtain information on the subject; and
a second measurement system including a detector and an information acquisition unit, the detector dividing the light output from the light source apparatus into measurement light and reference light and detects interfering light of the measurement light passing through the subject and the reference light, and the information acquisition unit of the second measurement system obtaining tomographic information on the subject based on information detected by the detector,
wherein the light source apparatus includes
a light source that generates first pulsed light; and
a nonlinear optical medium that generates second pulsed light having a wavelength different from a wavelength of the first pulsed light due to incidence of the first pulsed light,
wherein the light source is configured so that the first pulsed light has a center wavelength variable across a zero dispersion wavelength of the nonlinear optical medium.

12. The information acquisition apparatus according to claim 11, wherein the first measurement system is a microscope that detects: (i) light caused by stimulated Raman scattering based on molecular vibration of molecules in the subject; or (ii) light caused by coherent anti-Stokes Raman scattering.

13. The information acquisition apparatus according to claim 12, wherein the first measurement system further includes a synchronous detector that detects: (i) light caused by the stimulated Raman scattering based on the molecular vibration of the molecules in the subject; or (ii) light caused by the coherent anti-Stokes Raman scattering.

14. The information acquisition apparatus according to claim 11, wherein the information acquisition apparatus constitutes or comprises an endoscope apparatus.

15. The information acquisition apparatus according to claim 11, wherein the first pulsed light emitted from the light source apparatus has a pulse rate of 1 MHz or more and 1 GHz or less.

16. The information acquisition apparatus according to claim 11, wherein the second measurement system is an SD-OCT system.

17. The information acquisition apparatus according to claim 11, wherein the nonlinear optical medium satisfies following relations:

$\beta_2 > 0$ and $\beta_4 < 0$ on a short wavelength side with respect to $\lambda_0$; and $\beta_2 \leq 0$ on a long wavelength side with respect to $\lambda_0$, where $\lambda_0$ is the zero dispersion wavelength of the nonlinear optical medium, $\lambda_c$ is the center wavelength of the first pulsed light, $\beta_2$ is a group velocity dispersion of the nonlinear optical medium at the center wavelength $\lambda_c$, and $\beta_4$ is a second derivative of the group velocity dispersion $\beta_2$, wherein when information on the subject is to be obtained using the first measurement system, the center wavelength of the first pulsed light is set shorter than $\lambda_0$; and when tomographic information on the subject is to be obtained using the second measurement system, the center wavelength of the first pulsed light is set longer than $\lambda_0$.

18. The information acquisition apparatus according to claim 11, wherein the nonlinear optical medium satisfies following relations:

$\beta_2 > 0$ and $\beta_4 < 0$ on a short wavelength side with respect to $\lambda_0$; and $\beta_2 \leq 0$ on a long wavelength side with respect to $\lambda_0$, where $\lambda_0$ is the zero dispersion wavelength of the nonlinear optical medium, $\lambda_c$ is the center wavelength of the first pulsed light, $\beta_2$ is a group velocity dispersion of the nonlinear optical medium at the center wavelength $\lambda_c$, and $\beta_4$ is a second derivative of the group velocity dispersion $\beta_2$;

wherein when information on the subject is to be obtained using the first measurement system, the center wavelength of the first pulsed light is set longer than $\lambda_0$; and when tomographic information on the subject is to be obtained using the second measurement system, the center wavelength of the first pulsed light is set shorter than $\lambda_0$.

* * * * *